(12) United States Patent
Fries et al.

(10) Patent No.: US 7,674,581 B1
(45) Date of Patent: Mar. 9, 2010

(54) AUTONOMOUS GENOSENSOR APPARATUS

(75) Inventors: David P. Fries, St. Petersburg, FL (US); John H. Paul, St. Petersburg, FL (US); Andrew Farmer, St. Petersburg, FL (US); Matthew Smith, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 331 days.

(21) Appl. No.: 11/161,103

(22) Filed: Jul. 22, 2005

Related U.S. Application Data

(63) Continuation of application No. PCT/US2004/001666, filed on Jan. 22, 2004.

(60) Provisional application No. 60/441,876, filed on Jan. 22, 2003.

(51) Int. Cl.
*C12Q 1/68* (2006.01)
*C12M 1/36* (2006.01)
*G01N 15/06* (2006.01)

(52) U.S. Cl. .............. 435/6; 435/91.2; 435/283.1; 435/287.2; 435/288.4; 435/288.7; 422/68.1; 422/82.05

(58) Field of Classification Search ............ None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,876,187 | A | 10/1989 | Duck et al. |
| 5,030,557 | A | 7/1991 | Hogan et al. |
| 5,130,238 | A | 7/1992 | Malek et al. |
| 5,399,491 | A | 3/1995 | Kacian et al. |
| 5,409,818 | A | 4/1995 | Davey et al. |
| 5,437,990 | A | 8/1995 | Burg et al. |
| 5,485,184 | A | 1/1996 | Nakagomi et al. |
| 5,554,516 | A | 9/1996 | Kacian et al. |
| 5,554,517 | A | 9/1996 | Davey et al. |
| 5,866,430 | A * | 2/1999 | Grow ....................... 506/6 |
| 5,958,349 | A | 9/1999 | Petersen et al. |
| 6,187,530 | B1 * | 2/2001 | Scholin et al. ............ 435/4 |
| 6,200,531 | B1 | 3/2001 | Liljestrand et al. |
| 6,312,929 | B1 | 11/2001 | McMillan |
| 6,369,893 | B1 | 4/2002 | Christel et al. |

(Continued)

OTHER PUBLICATIONS

Fries et al. "In-water filed analytical tehcnology: Underwater mass spectrometry, mobile robots, and remote intelligence of wide and local area chemical profiling" Field Analytical Chemistry and Technology, 2001 5(3): 121-130.*

*Primary Examiner*—B J Forman
(74) *Attorney, Agent, or Firm*—Thomas E. Toner; Smith & Hopen, P.A.

(57) ABSTRACT

An autonomous genosensor apparatus and methods for use are provided for the field detection and analysis of ambient chemical, biochemical, biologic, biogenetic, and radiologic materials under field conditions in fluid or gaseous environments, such as marine or aquatic environments or industrial processes. Autonomous genosensors provide integral, self contained units which automatically extract environmental samples, prepare those samples for analytical studies, analyze those samples using studies such as DNA or biomarker analysis, and store or transmit the data produced to a remote computer or computer network. Autonomous genosensors may be used as freestanding units, or may be networked and controlled through a remote computer network.

22 Claims, 9 Drawing Sheets

U.S. PATENT DOCUMENTS

| | | |
|---|---|---|
| 6,374,684 B1 | 4/2002 | Dority |
| 6,403,037 B1 | 6/2002 | Chang et al. |
| 6,431,476 B1 | 8/2002 | Taylor et al. |
| 6,440,725 B1 | 8/2002 | Pourahamadi et al. |
| 6,534,645 B2 | 3/2003 | McMillan |
| 6,586,234 B1 | 7/2003 | Burg et al. |
| 6,664,104 B2 | 12/2003 | Pourahamadi et al. |
| 6,713,298 B2 * | 3/2004 | McDevitt et al. ......... 435/287.8 |
| 6,727,498 B2 * | 4/2004 | Fries et al. .................. 250/288 |
| 6,744,045 B2 * | 6/2004 | Fries et al. .................. 250/288 |
| 2002/0012612 A1 | 1/2002 | Siber et al. |
| 2002/0019060 A1 | 2/2002 | Petersen et al. |
| 2002/0025576 A1 | 2/2002 | Northrup et al. |
| 2002/0031768 A1 | 3/2002 | McMillan et al. |
| 2002/0034745 A1 | 3/2002 | McMillan et al. |
| 2002/0034746 A1 | 3/2002 | McMillan et al. |
| 2002/0039783 A1 | 4/2002 | McMillan et al. |
| 2002/0045246 A1 | 4/2002 | McMillan et al. |
| 2002/0045272 A1 | 4/2002 | McDevitt et al. |
| 2002/0058282 A1 | 5/2002 | McMillan et al. |
| 2002/0109844 A1 | 8/2002 | Christel et al. |
| 2002/0168299 A1 | 11/2002 | Chang et al. |
| 2002/0175079 A1 | 11/2002 | Christel et al. |
| 2002/0187547 A1 | 12/2002 | Taylor et al. |

* cited by examiner

100

*Karenia brevis* NASBA

AUTONOMOUS GENOSENSOR APPARATUS

CROSS REFERENCE TO RELATED APPLICATIONS

This application is a continuation of International Application No. PCT/US2004/001666, filed on Jan. 22, 2004, which claims the benefit of U.S. Provisional Patent Application Ser. No. 60/441,876 filed Jan. 22, 2003.

GOVERNMENT LICENSE RIGHTS

This invention was made in part under the sponsorship of Grant No. N00014-02-1-0265 awarded by the Office of Naval Research, United States Navy. The U.S. Government has retained rights in this invention.

FIELD OF INVENTION

The present invention relates generally to apparati and methods for molecular diagnosis, and relates more specifically to apparati and methods for the field detection and automatic analysis of ambient nucleic acid or other biomarkers in a marine or aquatic environment.

BACKGROUND OF THE INVENTION

Molecular diagnostic methods have become a commonplace tool not only in human genetics, but in microbial genomics, fungal genomics, and mammalian genomics. This is due to advances in DNA/RNA extraction techniques, sequencing methods, amplification techniques, simpler detection methods and the introduction of semiautomated instruments.

The measurement of genetic transcription and gene production by real-time amplification methods are increasingly being used to investigate microbes and biological organisms. However, traditional protocols typically require laboratory analysis and a separation between sample collection and analysis.

In marine waters and other difficult matrices, sample preparation and extraction is key to successful noise and interference reduction and signal enhancement. For capture and purification of target nucleic acids from natural samples it is essential to utilize an efficient binding material that has high selectivity. A material of initial choice is solid phase specific or non-specific binding surface materials. The material can be suitable for irreversible binding of single stranded DNA and RNA and permits capture, isolation, and potential amplification of the captured nucleic acids directly on the solid phase using any amplification strategy. The material can be derivatized with specific oligonucleotides for added capture specificity where few copies of targets are present in complex matrix. The material also provides archiving capability in case samples need to be brought back to the lab for further analysis.

Molecular beacons are oligonucleotide probes that become fluorescent upon hybridization, thus signaling the presence of nucleic acids in solutions and monitoring the synthesis of amplified products in amplification reactions. Employing existing technology, it is possible to engineer different probe beacons having different colored wavelength emissions so that multiple targets can be simultaneously detected allowing for multiplexed assay and internal quality controls. Also since the probes may be engineered differently, probes can be made for any of the manifold biospecies existing in nature.

Devices and reaction vessels or other containers for the lysis of cells, viruses, macromolecules, particles, or other components within a sample are disclosed in U.S. Pat. Nos. 5,958,349; 6,369,893; and 6,431,476 and U.S. Patent Application Publication Nos. US 2002/0039783, US 2002/0045246, US 2002/0109844, US 2002/0168299, and US 2002/0187547, (which are hereby incorporated by reference in their entirety).

U.S. Pat. No. 6,586,234 (which is hereby incorporated by reference in its entirety) discloses a device for separating an analyte, including nucleic acids, from a fluid sample comprises a cartridge incorporating a flow-through microfluidic chip. As disclosed therein, the cartridge may optionally include a lysing region for lysing sample components (e.g., cells spores, or microorganisms), a waste chamber for storing waste fluid, and reaction or detection chambers for amplifying or detecting the analyte. According to the '234 Patent, this technique allows the entire processing facility to be small, yet capable of processing relatively large fluid samples (e.g., 0.1 to 10 mL).

Nucleic acid amplification technology is well known, and is discussed in documents including U.S. Pat. Nos. 4,683,195; 4,683,202; 5,130,238; 4,876,187; 5,030,557; 5,399,491; 5,409,818; 5,485,184; 5,409,818; 5,554,517; 5,437,990; 5,554,516; 6,312,929; 6,534,645; and 6,586,234 and U.S. Patent Application Publication Nos. US 2002/0034745, US 2002/0058282, US 2002/0031768, and US 2002/0034746 (each of which are hereby incorporated by reference in their entirety). It is well known that methods such as those described in these patents permit the amplification and detection of nucleic acids without requiring cloning, and are responsible for the most sensitive assays for nucleic acid sequences. It is further known that computer programs may be employed to provide a highly reproducible quantitative analysis of a nucleic acid amplification reaction.

The use of flow-through microfluidic chips to separate an analyte from a fluid sample was disclosed in U.S. Pat. No. 6,664,104 (which is hereby incorporated by reference in its entirety), which teaches the combination of a cartridge containing such a chip with an optional lysing region, waste chamber for storing waste fluid, and reaction or detection chambers for amplifying or detecting the analyte.

A reaction vessel in combination with a temperature control system for performing heat-exchanging chemical reactions such as nucleic acid amplification is disclosed by U.S. Pat. No. 6,403,037 (which is hereby incorporated by reference in its entirety). A reaction vessel for holding a sample for a heat-exchanging chemical process such as polymerase chain reaction is taught by U.S. Pat. No. 5,958,349 (which is also hereby incorporated by reference in its entirety).

Chips with non-planar microstructures have also been used to manipulate materials including particles, cells, macromolecules, proteins, nucleic acids, and other moieties in fluid samples according to U.S. Pat. No. 6,368,871 (which is hereby incorporated by reference in its entirety).

Other systems for the manipulation and processing of fluid samples is disclosed by U.S. Pat. Nos. 6,374,684 and 6,440,725 and U.S. Patent Application Publications US 2002/0019060, US 2002/0025576, US 2002/0012612, and US 2002/0175079 (which are hereby incorporated by reference in their entirety).

The foregoing known technologies provide a means for the analysis of an analyte in a fluid or gaseous medium, but do so only in a laboratory setting, with the need for a human operator to control the detection and analysis processes. In many potential applications, particularly in the fields of environmental research, biochemical warfare, hazardous matter situations, and space research, it would be advantageous to develop compact, self-contained analyzers that could autonomously detect and analyze chemical, biochemical, radiologic, or biogenetic expression activity under deployed field conditions to perform specimen collection and concurrently provide real-time analysis of those specimens.

More specifically, the need exists for a system to detect target microorganisms and larger biological organisms in both the marine and fresh water environments, as well as sources of drinking water or in any industrial process that may have microbial content concerns. It would be additionally desirable for such a system to provide for the automatic and autonomous detection and analysis of target gene sequences from desired organisms and further provide for the transmission of the data generated to remote data collection centers in near real time. Sample amplification in such a system would also be desirable, and could be performed using any of the existing nucleic acid amplification methods currently commercially available specifically, PCR-Polymerase Chain Reaction, RT-PCR-Reverse Transcription PCR, and NASBA-Nucleic Acid Sequence Based Amplification (NASBA) method.

SUMMARY OF THE INVENTION

The present invention is directed to an autonomous genosensor apparatus or system and method for use, in which automated sample collection is combined with a nucleic acid amplification and or other biomarker reactor with molecular probe beacons toward targeted environmental problems.

The invention is a fully functioning system that is at least selectively open to the environment in which it is deployed for automatic mass transfer of environmental biological material for subsequent identification of biological species-specific biomarkers using a process of joined subsystems of biomarker extraction, biomarker amplification or replication and biomarker detection. The combination of the interacting and interrelated subsystems into an integral unit that performs automatic, in-situ observation of targeted biological material. The autonomous genosensor system is additionally open to tuning and reconfiguration for detection of different biological materials through the design and engineering of species-specific recognition probes that are an integral part of the detector subsystem.

In an exemplary aspect according to the present invention, an autonomous system is provided for the detection and identification of microorganisms or molecular biological materials in a marine or aquatic environment or in mixed fluid/solid environments such as boreholes and subsurface sediment.

In another exemplary aspect according to the present invention, an autonomous genosensor automatically detects the presence of and analyzes gene sequences from desired target organisms ambient within a marine or aquatic environment, and then transmits the analysis data to remote data collection centers in near real time.

In still other exemplary aspects according to the present invention, autonomous genosensors may be deployed in a standalone fashion, or as distributed networked arrays, or as payloads on autonomous underwater vehicles, remotely operated vehicles, and other robotic or manned vehicles and watercraft.

In yet other exemplary aspects according to the present invention, autonomous genosensors may include miniaturized subsystems or the autonomous genosensor system as a whole may be connected to appendages that permit sampling of different media (e.g. subsurface sediment sampling).

In yet other exemplary embodiments, autonomous genosensors may include reactors and detectors suitable for the detection and analysis of physical chemical, biochemical, radioactive, and other biological materials using real-time sample collection, analysis, and data communication aspects according to the present invention.

Additional embodiments anticipated according to the present invention include the capacity for in situ hybridization analysis bf targeted nucleic acids.

Other aspects according to the present invention further anticipate that the autonomous genosensor system's subsystems or entire autonomous genosensor system may be provided in the form of an integrated chip, microchip, or MEMS system, or packaged as a total analysis printed wiring assembly, or fitted with a fluidic probe stinger, and/or any combinations of the foregoing.

Such an exemplary systems according to the present invention may be self-powered, or they may be powered by any available power supply.

The present invention and methods for its use anticipate many alternate embodiments in other potential applications in the broad fields of biology and environmental science and process control. The discussions herein are intended to be exemplary embodiments according to the present invention, and should not be construed to limit the present invention and methods for use in any way.

Objects, features, and advantages of the present invention will become apparent upon reading the following specification, when taken in conjunction with the drawings and appended claims.

DETAILED DESCRIPTION

In an exemplary embodiment according to the present invention, an autonomous genosensor is fully incorporated within a housing with sample intake ports and sample egress ports that connect with a sample manager to move a sample within the housing. Also within the housing of an exemplary autonomous genosensor, a preconcentrator/extractor processes the sample, and may perform filtration, concentration, and/or analysis of the sample. A reactor then receives a sample from the sample manager and contains the sample during a chemical, biochemical, or biologic reaction. The reactor may be combined with a biomarker amplifier in various embodiments as anticipated according to the present invention. The reactor is in communication with a detector that then detects an analyte within the sample. All functions and movement within the housing is under the control of an electronic control system which is powered by a power supply, also contained within the housing.

In an exemplary method of use of an autonomous genosensor according to the present invention, a targeted analyte in a fluid or gaseous environment is detected and analyzed by first deploying an autonomous genosensor into the fluid or gaseous environment and operating the autonomous genosensor to collect ambient fluid or gaseous samples. By reacting these samples with reagents specific to a targeted analyte to permit amplification of the analyte, optical detecting of the targeted amplified analyte is achieved, and the analytical data is electronically stored or transmitted.

Figure 1:
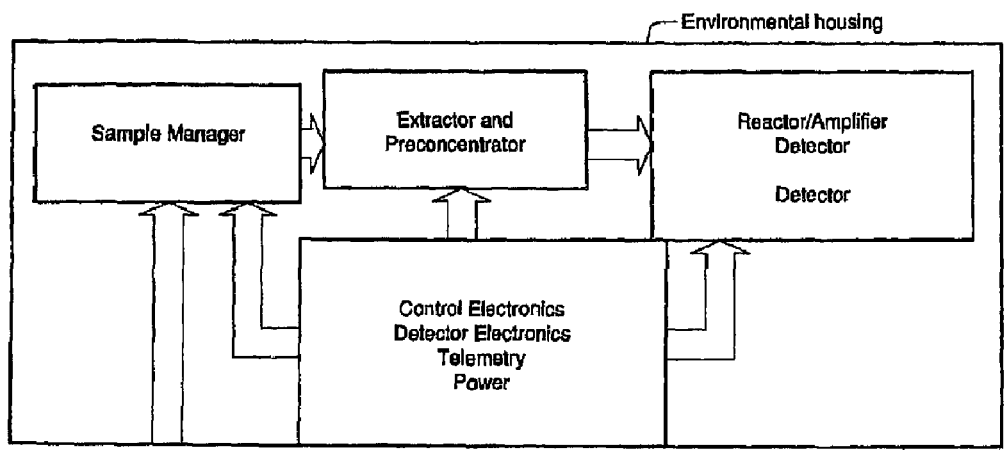
FIG. 1 shows a schematic diagram of an embodiment of an autonomous genosensor according to the present invention.

An operational schematic diagram of an exemplary embodiment according to the present invention is shown in FIG. 1. Contained within a housing that is at least selectively open to the environment, the autonomous genosensor according to the present invention provides an autonomous biomarker detection system that permits automatic mass transfer of biological material for in-situ detection of ambient chemical, biochemical, biologic, biogenetic, and radiologic materials under field conditions. According to FIG. 1, an autonomous genosensor according to the present invention provides a sample manager that admits samples within the housing, and conveys the samples through a preconcentrator/extractor for preconcentration and extraction processes before delivering the samples to a reactor for a desired reaction. During or after that reaction, the samples are analyzed by a detector that is controlled by an electronic control that is powered by a power supply contained within the housing.

Figure 2:
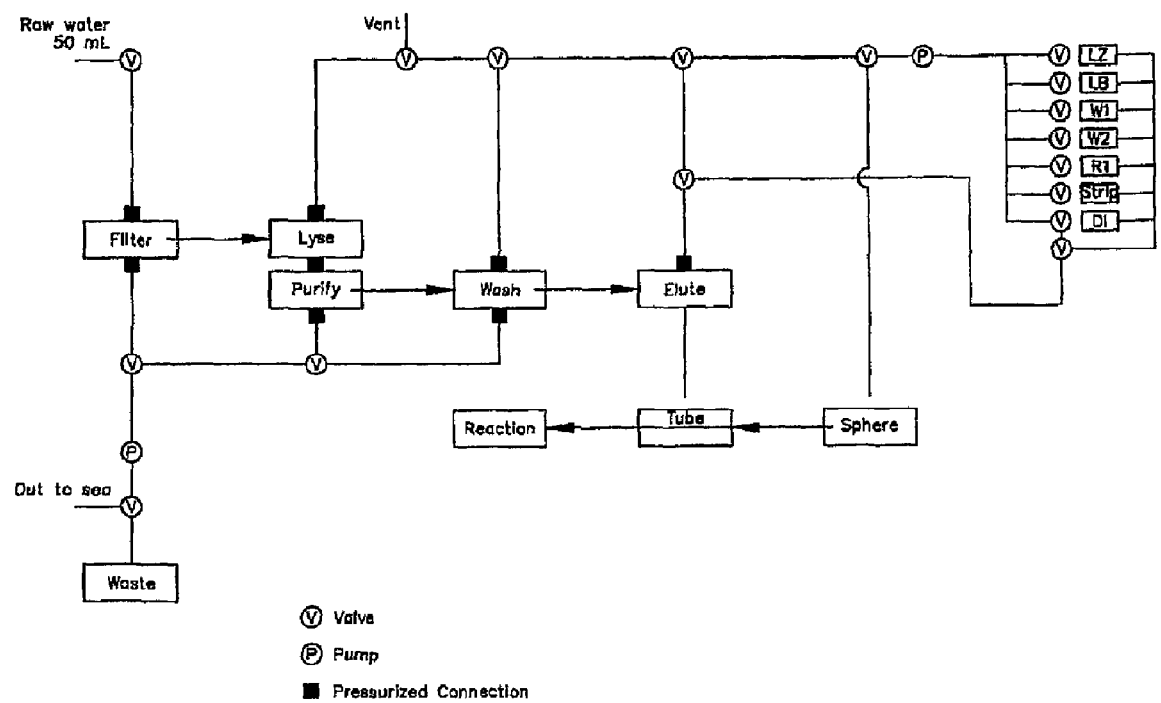
FIG. 2 shows a schematic diagram of another embodiment of an autonomous genosensor according to the present invention.

A fluidic logic or operational schematic diagram of the components of an exemplary embodiment of an autonomous genosensor according to the present invention is shown in FIG. 2. Employing a series of valves and pumps, a sample is brought into the housing of an autonomous genosensor through an intake port. As it is transported through a sample manager, the sample is filtered, lysed, and purified in a preconcentrator/extractor. The sample is placed within a reactor in which a reaction with reagents occurs. Following the reaction, the sample is analyzed by a detector, and the waste and sample is then removed from the autonomous genosensor through an egress port.

Figure 3:
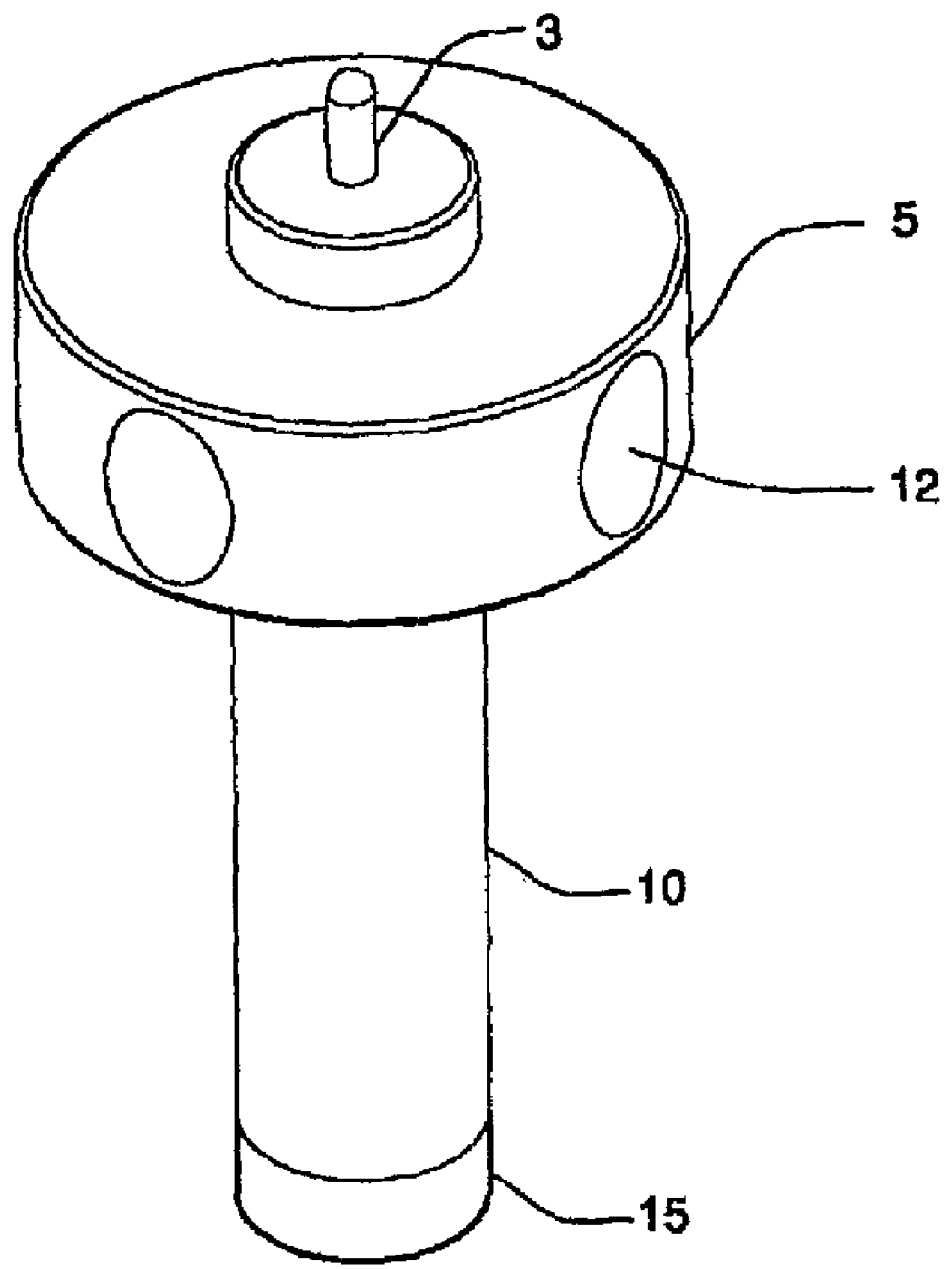
FIG. 3 shows a first embodiment of an autonomous genosensor, showing the overall unit contained within a housing in a floating deployment in a water environment.

Referring now to the drawings, in which like numerals indicate like elements throughout the several views, an exemplary autonomous genosensor system 100 comprising a housing 10 is shown in FIG. 3. In various embodiments according to the present invention, the housing may be fabricated of any solid material, including but not limited to, metals, metal alloys, plastics, natural or synthetic rubbers, and ceramics. In a preferred embodiment according to the present invention, the housing is constructed of titanium or titanium alloys to provide structural protection for the contents of the housing at greater depths beneath the ocean. In addition, in a preferred embodiment according to the present invention, the housing is constructed to be waterproof to provide protection to its contents when submerged below water in a marine or aquatic environment or to maintain internal pressurization under environments of extremely high or low pressure.

In the exemplary embodiment according to the present invention shown in FIG. 3, the housing 10 is an elongated cylinder defining further an upper end 5 and a lower end 15. In various embodiments according to the present invention, the upper end 5 may be flared, flattened, or otherwise of greater diameter than the lower end 15 to allow the upper end 5 to float on or near the water surface.

In various embodiments according to the present invention, the lower end 15 may be weighted to keep the autonomous genosensor 100 upright in the water, and to allow for self-righting by the autonomous genosensor 100 in the course of wave or current flow dynamics. The housing 10 may further be provided with one or more intake/egress ports 12 to allow water intake or egress by the autonomous genosensor 100 for sampling and analytical purposes. The exemplary autonomous genosensor 100 in FIG. 1 is further shown with a LAN antenna 3, providing a means of wireless communications between the autonomous genosensor 100 and a remote networked computer system (not shown in FIG. 3) to allow data exchange, transfer, and remote control of certain device functions, including provision for support using communications with a global positioning satellite system to identify and maintain exact autonomous genosensor location.

Figure 4:
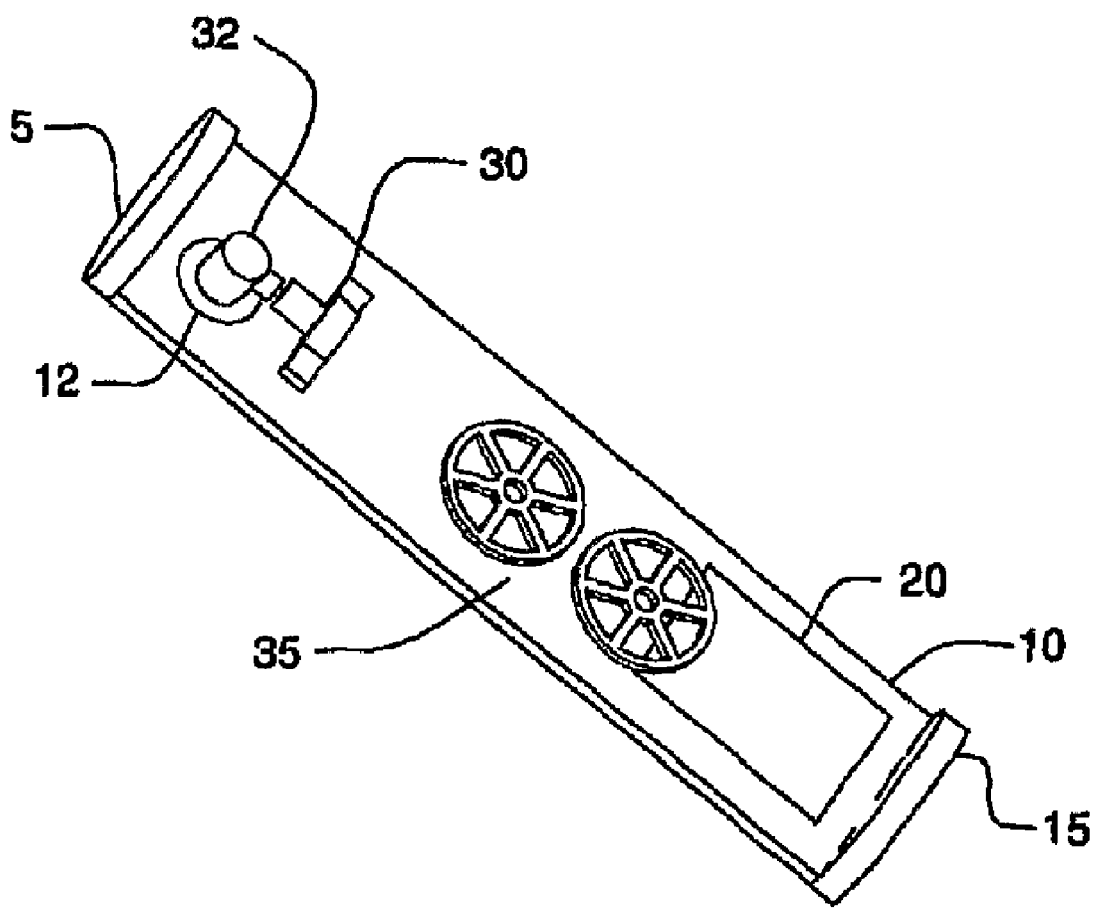
FIG. 4 shows a partial longitudinal cross-sectional view of the autonomous genosensor of FIG. 2, showing the relationship of its components.

FIG. 4 shows another view of an embodiment of an autonomous genosensor 100 according to the present invention, in which the housing 10 has been partially removed to show a longitudinal cross-section of the housing's contents. At the upper end 5, intake and egress ports 12 are provided for water intake and release. The intake and egress ports 12 are in direct communication with one or more pumps 32 which serve to cause water intake or release from the system. The intake and egress ports 12 are further connected to valves (non shown) to control water flow directional control. In addition, the intake and egress ports 12 are in direct communication with the fluidic manifold with valves and pump 30, which serves as a sample manager to direct water intake and egress by the analytical systems. The exemplary autonomous genosensor of FIG. 3 is further provided with a preconcentrator/extractor in the form of a tape drive unit 35 which serves to package the diagnostic material for sequential operation in a reel-to-reel format similar to a linear tape drive mechanism. This permits the substantial storage capacity of tape in a very compact assembly.

In alternate embodiments according to the present invention, the preconcentrator/extractor may employ reaction tubes or other containers with stacked modular discs to provide sample extraction and concentration, rather than the tape drive configuration discussed above. Such an alternate embodiment is shown in FIGS. 4-9.

FIG. 4 also shows the location of a power supply 20, located towards the lower end 15 of the autonomous genosensor unit 100. In various embodiments according to the present invention, the power supply 20 may comprise batteries, power cells, a self-contained generator, or solar, thermal, or other electrical generating means with or without a storage means for the energy generated. In the various embodiments according to the present invention, the power supply 20 may provide power to the pumps 32, the fluidic manifold 30, the tape drive 35, or the control systems (not shown) that regulate the various components of the autonomous genosensor 100.

Figure 5:
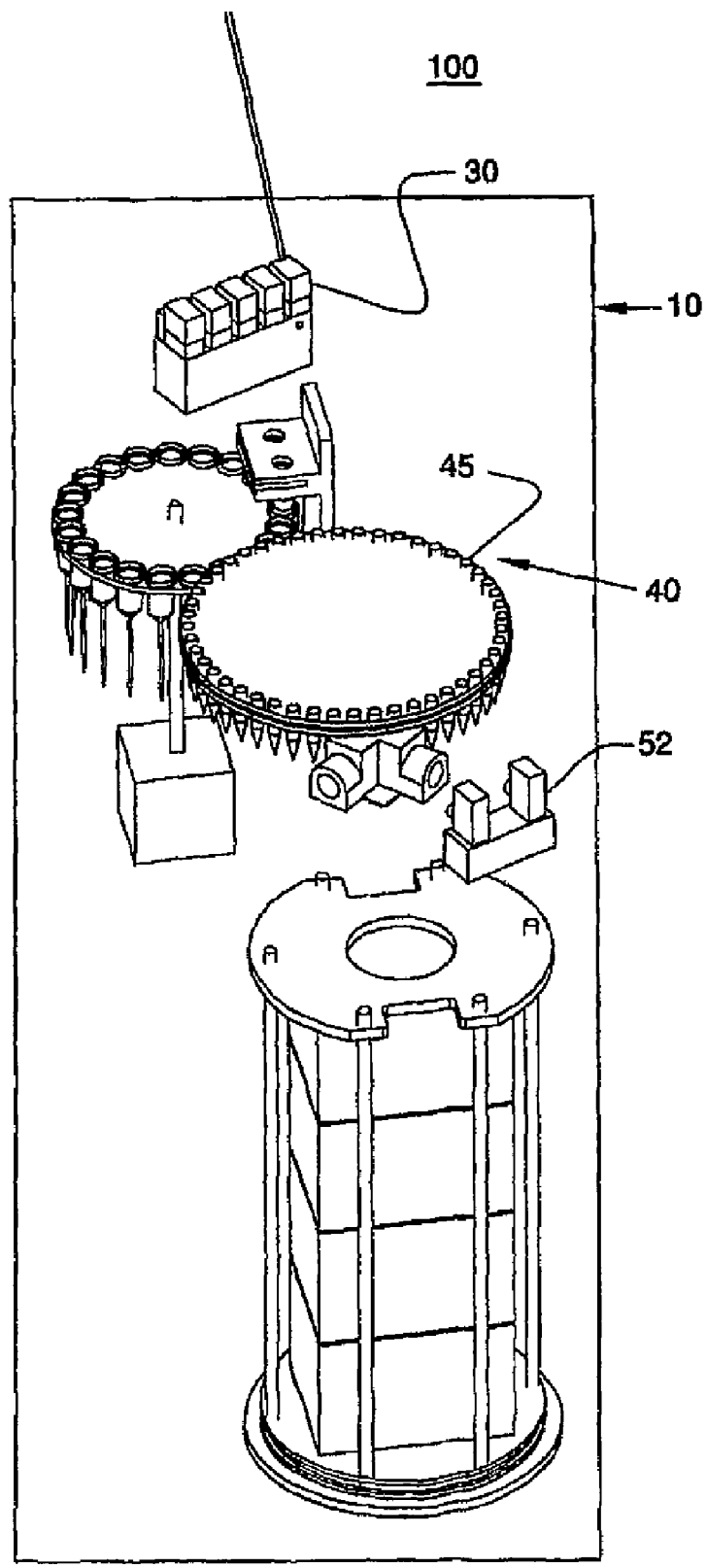
FIG. 5 shows a partially exploded side view of the internal components of a embodiment of an autonomous genosensor according to the present invention.

FIG. 5 shows a partially exploded side view of the components of the interior of an embodiment of an autonomous genosensor according to the present invention. Fluid samples acquired by the system are manipulated through the sample manager represented by the fluidic manifold with pumps and valves 30 and placed into a preconcentrator/extractor, which in this embodiment is provided as an array of reaction tubes 45. The array of reaction tubes 45 is rotated through the reactor, shown in the embodiment of FIG. 5 as a reactor/detector chamber 40, where the analytical portion of the process occurs. Peristaltic pumps 52 may be employed in various embodiments according to the present invention to regulate incoming fluids into the reaction chamber 40 to prevent retrograde flow. In various other embodiments anticipated 5 according to the present invention, other pumps or needle injectors may be used in place of the peristaltic pumps 52.

Figure 6:
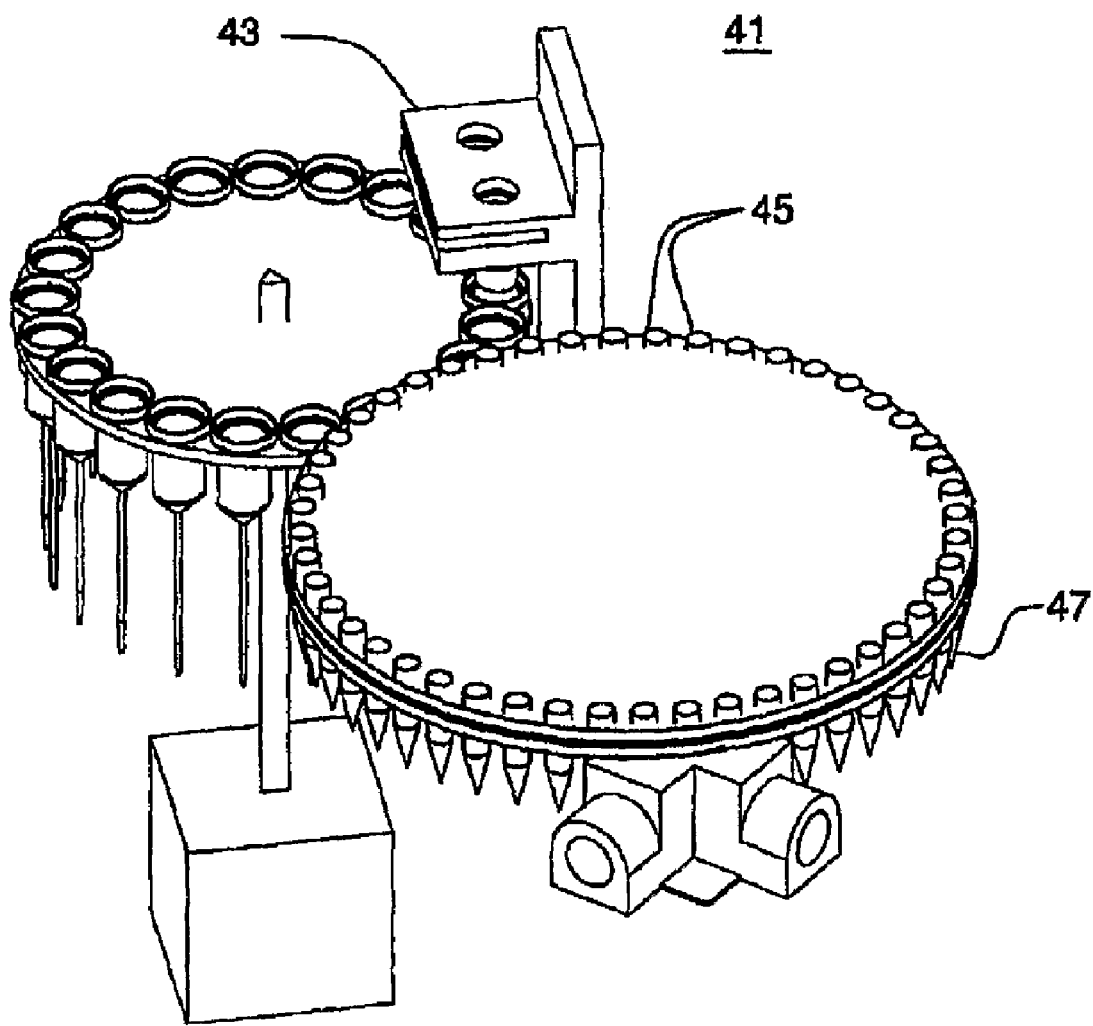
FIG. 6 shows a detail of the reaction tube array and reactor/detector chamber assemblies of an embodiment of an autonomous genosensor according to the present invention.

FIG. 6 shows an amplified detail of the preconcentrator/extractor, with a filtration/purification assembly 41 and reaction tube array 45. Fluid 10 samples are dispensed from the intake ports 12 (shown in previous figures) and pass through the fluidic manifold with pump and valves 30 (also shown in previous figures), and are dispensed by the fluid dispenser 43 into reaction tubes 45 which contain stacked silica meshed discs 47. The silica meshed discs 47 act to concentrate materials from the incoming fluid.

Figure 7:
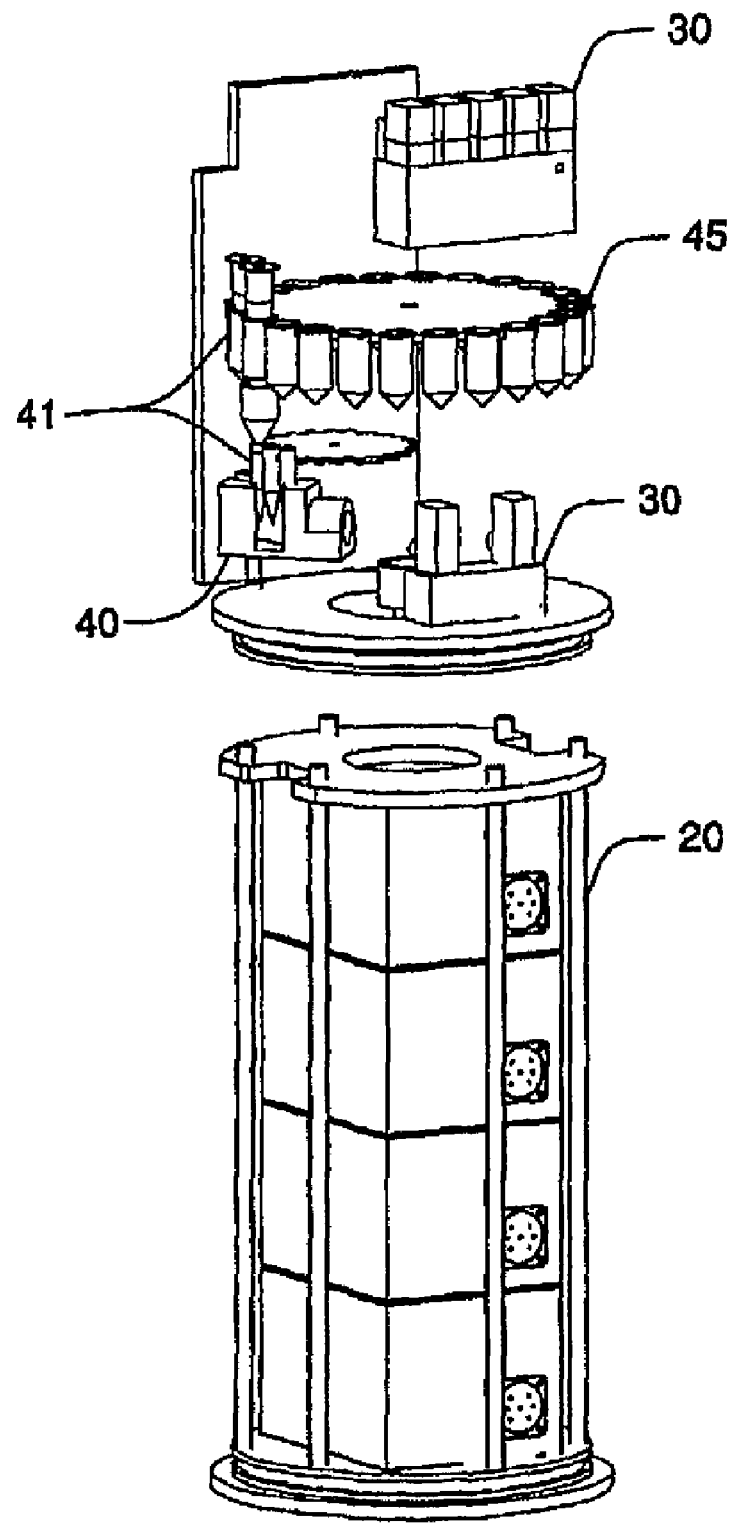
FIG. 7 shows a view of the internal components of an alternate embodiment of an autonomous genosensor according to the present invention.

FIG. 7 shows the relationship between the fluidic manifold with pumps and valves 30, filtration/purification assembly 41 and reaction tube array 45, reactor/detector chamber 40, and the battery/power supply 20 in one embodiment according to the present invention. FIG. 7 also shows its various components in the form of an integral assembly which when combined with an environmental protection housing is amenable to deployment within a gas, fluid, or mixed water/solid environments.

Figure 8:
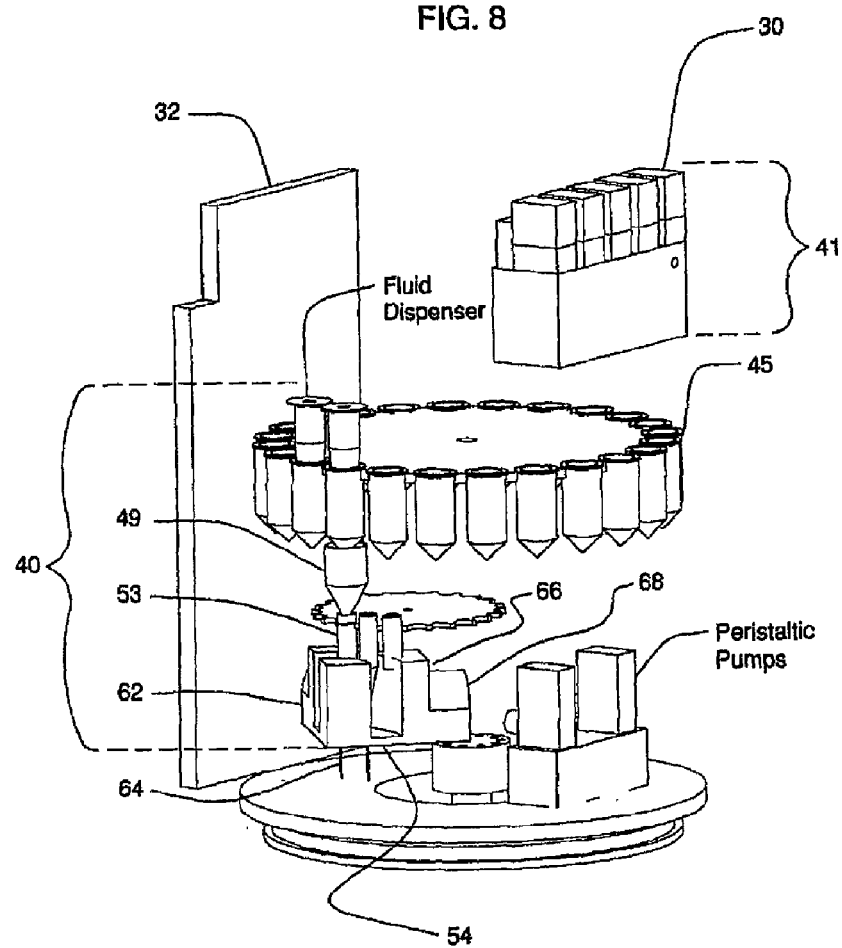
FIG. 8 shows a detailed view of the sample manager and reactor/detector components of an alternate embodiment of an autonomous genosensor according to the present invention.

FIG. 8 shows a detailed view of the relationships among the sample manager and reactor/detectors in an embodiment according to the present invention. The components in FIG. 8 are mounted along with the main board 32 onto structural support elements (not shown) which provides physical support for the fluidic manifold with pumps and valves 30, filtration/purification assembly 41 and reaction tube array 45, and the reactor/detector chamber 40. Also detailed are the waste tubes 49 which receive waste fluid, and the optical tubes 53 which contain the specimens within the optical block 54.

Figure 9:
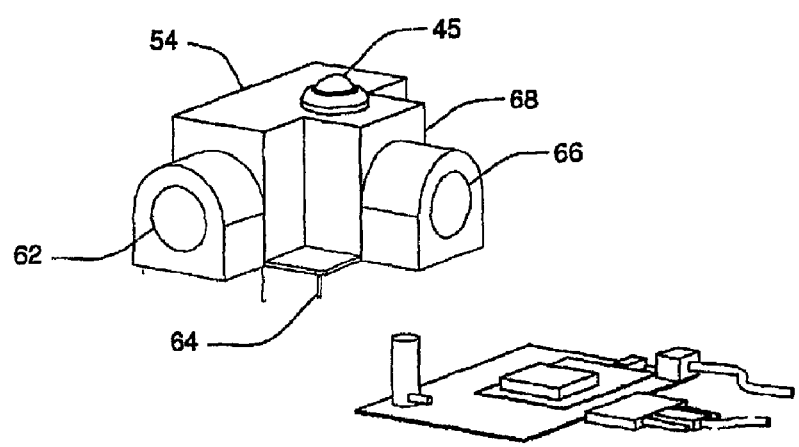
FIG. 9 shows a detailed view of the infrared heater and sensor components of an alternate embodiment of an autonomous genosensor according to the present invention.

A detector in an exemplary embodiment according to the present invention is shown in FIG. 9 and includes an optical block 54, an infrared sensor 62, an infrared heater 64, a light emitting diode (LED) 66, and a fluorometer 68, which is electronically connected to both the LED 66 and the infrared heater 64. Within the optical block 54, the infrared heater 64 brings the reaction tube 45 to the necessary temperature for the desired reaction to occur, and the fluorometer 68 serves to detect fluorescence in processes familiar to one skilled in the art such as NASBA or fluorescent molecular beacon analysis.

In the case of nucleic acid analysis, in various embodiments according to the present invention, amplification is performed using any of the existing nucleic acid amplification methods currently commercially available specifically, PCR-Polymerase Chain Reaction, RT-PCR-Reverse Transcription PCR, and NASBA-Nucleic Acid Sequence Based Amplification (NASBA) method. Alternately, according to the present invention, a detector for amplicon detection is employed in real-time via the use of florescent molecular beacons and or fluorescent resonant energy transfer (FRET) probes. The required reagents used can be either in liquid form or dry pellets to enable a compact design.

In other alternative embodiments according to the present invention, nucleic acid amplification technology and embedded probe Molecular Beacons are combined in a modified manner for unattended field deployment.

Unlike the previously existing technologies, the autonomous genosensor combines the functionalities of a tape drive or stacked modular discs, solid phase extractor, amplification/fluorescence reactor cell, and fluorescence molecular beacon transducers to produce a compact, automated single-step system for micro and biological organism DNA/RNA extraction, amplification, and detection and molecular gene expression characterization.

An integrated heating and optical cell is employed in various embodiments according to the present invention for fluorescence detection of the amplification products. In an application according to the present invention, the detector is a filter-based fluorometer, with the filter tuned to the fluorophores on the beacon transducers. The small light source employed can alternately be a sufficiently bright LED or laser tuned to the wavelength of the fluorophores (e.g. 635 nm diode laser and Cy5 fluor). In most applications, the laser should yield a higher fluorescence signal. The beacon provides the advantage of allowing real-time detection throughout the amplification cycle. The reactions can be monitored alternately after stopped flow or during flow.

Another embodiment is the use of a linear tape made of solid phase extraction and concentration material which permits an alternate detection approach using detection of the fluorescence from the reactions occurring on the surface of the tape material. The exposed fluorescent hybrid beacon spot on the tape surface is analyzed using, for example, an inexpensive 45° fluorescent reader that reads the fluorescence from the surface bound amplified products that have reacted to embedded molecular recognition probes. In such embodiments according to the present invention, the reader comprises an LED, prism guide, lens and filter, and detector chip. The signal from this output can then be compared to the solution signals to assess the level of bound to unbound beacon. Fluid flow is provided by any compact pressurized pumping scheme in such alternate embodiments.

The present invention as disclosed herein further comprises the use of amplicon detection in real-time via the use of fluorescent molecular beacons and or FRET fluorescent resonant energy transfer probes. The required reagents used may be either in liquid form or dry pellets to enable a compact design.

In other exemplary embodiments according to the present invention, the detector used to detect and analyze analytes in fluid or gas samples employs other chemical or non-chemical labeling technologies, including, but not limited to, radionuclide labeling technology.

EXAMPLES

Figure 10:
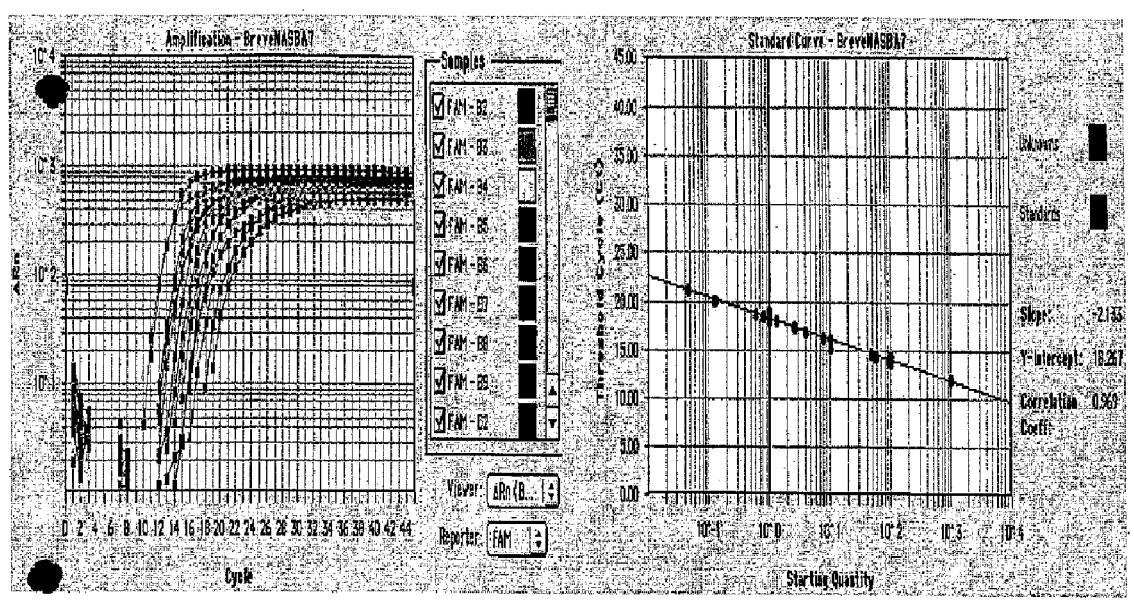
FIG. 10 shows exemplary data collected using the present invention to detect and analyze Karenia brevis in sea water.
Figure 11:
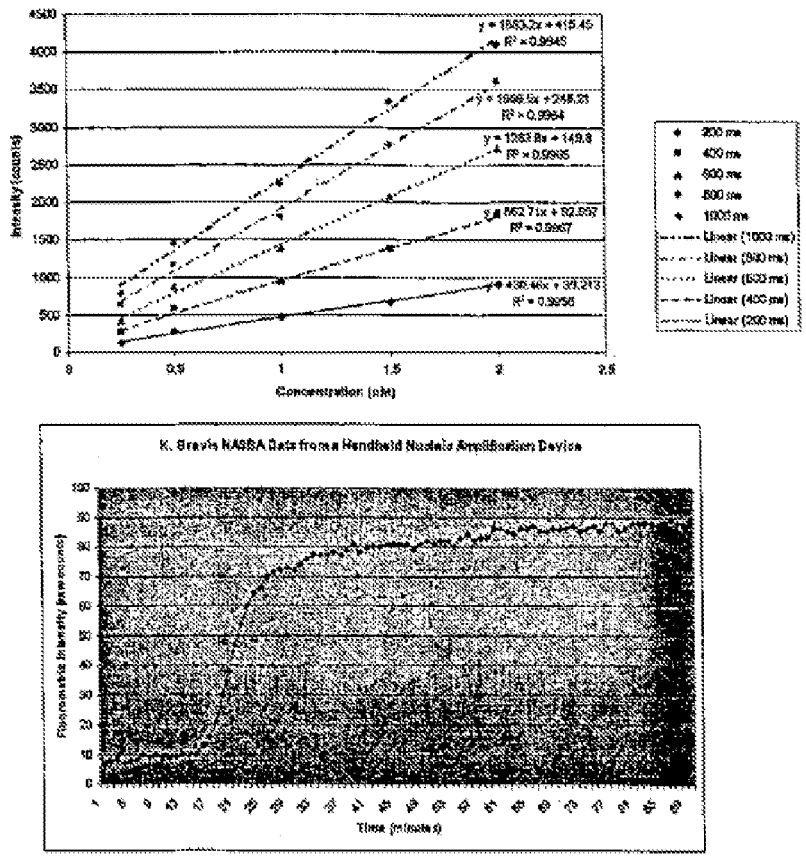
FIG. 11 shows exemplary data collected using the present invention to detect and analyze Karenia brevis and Enterovirus in sea water.
Figure 11:
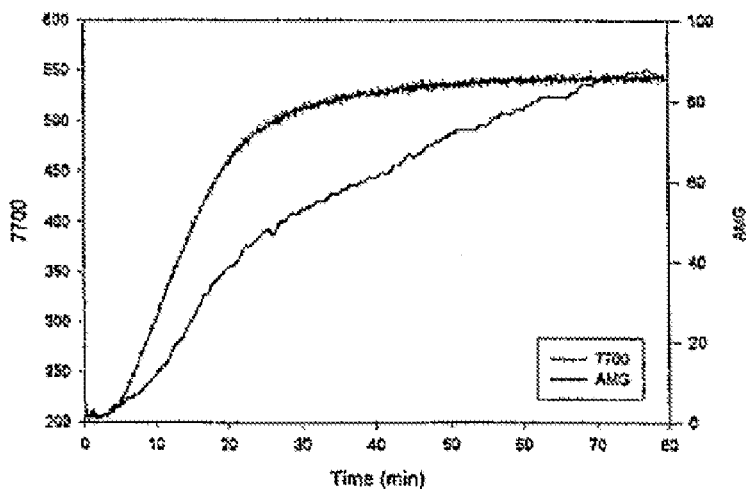

FIGS. 10 and 11 contain research data obtained using an embodiment of the present invention to detect and analyze Karenia brevis and Enterovirus in sea water.

What is claimed is:
1. An autonomous genosensor, comprising:
a water-tight sealed housing having one or more sample intake ports and one or more sample egress ports, wherein the housing is sealed to allow operation while partially or totally immersed in a liquid or gaseous environment;

a sample manager within said housing in communication with said intake port for moving the sample through the housing;

a reactor within said housing in communication with said sample manager for containing the sample during a chemical, biochemical, or biologic reaction, in which the reactor further comprises a nucleic acid amplification system;

a nucleic acid detector within said housing in communication with said reactor for detecting an analyte in the sample within the reactor;

an electronic control system within said housing in electrical communication with the detector, the reactor, and the sample manager for controlling the movement of samples through the housing and for controlling the reaction and detecting the reactions within said housing, wherein the electronic control system is capable of automatic operation; and a power supply within said housing in electrical communication with the reactor, the detector and the electronic control system.

2. The autonomous genosensor of claim 1, in which the sample manager further comprises a fluidic manifold.

3. The autonomous genosensor of claim 1, in which the sample manager further comprises a preconcentrator and extractor assembly.

4. The autonomous genosensor of claim 3, in which the preconcentrator and extractor further comprises a tape drive unit to package specimens within the samples for diagnostic study in sequential operation in a reel-to-reel format.

5. The autonomous genosensor of claim 3, in which the preconcentrator and extractor further comprises reaction containers with stacked modular discs to provide sample extraction and concentration.

6. The autonomous genosensor of claim 1, in which the detector further comprises:
   an optical block; and
   a fluorometer.

7. The autonomous genosensor of claim 1, in which the detector further comprises a system to perform fluorescent molecular beacon analysis.

8. The autonomous genosensor of claim 1, in which the detector employs a fluorescent resonant energy transfer probe to detect a nucleic acid in the analyte.

9. The autonomous genosensor of claim 1, in which the reactor and/or the detector further comprises a controlled heater to produce and maintain a necessary temperature for a desired reaction to occur.

10. The autonomous genosensor of claim 1, in which the power supply further comprises an electrical energy generating device selected from the group consisting of one or more batteries, power cells, self-contained electrical generators, solar generators, or thermal generators.

11. The autonomous genosensor of claim 1, further comprising one or more pumps or injectors to manipulate fluid samples and/or to regulate the flow of fluids into and away from said reactor or detector.

12. The autonomous genosensor of claim 1, further comprising a transmitter electronically integrated with said detector and electronic control system, such that electronic signals generated by said detector are transmitted to a remote receiver to allow data transfer.

13. The autonomous genosensor of claim 1, in which said housing is fabricated of a material selected from the group consisting of metals, metal alloys, plastics, natural rubbers, synthetic rubbers and ceramics.

14. The autonomous genosensor of claim 1, in which said housing is configured and weighted to keep the autonomous genosensor upright in a fluid environment, and to allow for self-righting by the autonomous genosensor in the course of wave or current flow dynamics.

15. The autonomous genosensor of claim 14, in which said housing is further configured so that said autonomous genosensor is capable of floating at or near the surface of said fluid environment.

16. The autonomous genosensor of claim 1, wherein the housing has an upper end and a lower end, the upper end having a greater extent than the lower end to facilitate floating on or within a liquid medium.

17. The autonomous genosensor of claim 16, wherein the upper end is flattened or flared relative to the lower end, the flattened or flared shape allowing the genosensor to float in an upright orientation within the liquid medium.

18. The autonomous genosensor of claim 16, wherein the lower end is weighted to facilitate floating in an upright orientation within the liquid medium.

19. The autonomous genosensor of claim 1, wherein the genosensor is buoyant to facilitate floating on or within a liquid medium.

20. The autonomous genosensor of claim 1, wherein the nucleic acid detector is a sequence-specific nucleic acid detector.

21. The autonomous genosensor of claim 1, in which the sample manager further comprises an extractor assembly, wherein the extractor assembly lyses and purifies the cellular content of the sample.

22. The autonomous genosensor of claim 1, wherein the nucleic acid amplification system employs tagged biomolecules in the amplification process to facilitate the detection of a target analyte.

* * * * *

UNITED STATES PATENT AND TRADEMARK OFFICE
CERTIFICATE OF CORRECTION

| | | |
|---|---|---|
| PATENT NO. | : 7,674,581 B1 | Page 1 of 1 |
| APPLICATION NO. | : 11/161103 | |
| DATED | : March 9, 2010 | |
| INVENTOR(S) | : David P. Fries et al. | |

It is certified that error appears in the above-identified patent and that said Letters Patent is hereby corrected as shown below:

In the Specification

Column 1, lines 11-16, should read: GOVERNMENT LICENSE RIGHTS

This invention was made with government support under Grant Number N00014-02-1-0265 awarded by the Office of Naval Research. The government has certain rights in the invention.

Signed and Sealed this
Seventh Day of October, 2014

Michelle K. Lee
*Deputy Director of the United States Patent and Trademark Office*